(12) United States Patent
Schade et al.

(10) Patent No.: US 7,465,774 B1
(45) Date of Patent: Dec. 16, 2008

(54) USE OF COPOLYMERS OF CARBOXYLIC ACIDS AND LONG-CHAIN COMPOUNDS WITH ISOLATED C-C MULTIPLE BONDS AS THICKENERS OR DISPERSANTS

(75) Inventors: Christian Schade, Ludwigshafen (DE); Axel Sanner, Frankenthal (DE); Hans-Ulrich Wekel, Ellerstadt (DE); Franz Frosch, Bad Duerkheim (DE); Horst Westenfelder, Neustadt (DE)

(73) Assignee: BASF Aktiengesellscahft, Ludwigshafen (DE)

( * ) Notice: Subject to any disclaimer, the term of this patent is extended or adjusted under 35 U.S.C. 154(b) by 0 days.

(21) Appl. No.: 08/325,219

(22) PCT Filed: Apr. 14, 1993

(86) PCT No.: PCT/EP93/00903

§ 371 (c)(1), (2), (4) Date: Oct. 21, 1994

(87) PCT Pub. No.: WO93/22357

PCT Pub. Date: Nov. 11, 1993

(30) Foreign Application Priority Data

Apr. 23, 1992 (DE) .................................... 4213283

(51) Int. Cl.
*C08F 220/06* (2006.01)
(52) U.S. Cl. ............... 526/318.3; 526/318.5; 524/556; 524/558; 524/563
(58) Field of Classification Search .............. 526/318.3, 526/318.5; 524/556, 558, 563
See application file for complete search history.

(56) References Cited

U.S. PATENT DOCUMENTS

| 2,945,013 | A | * | 7/1960 | Ott | .......................... 526/318.5 |
| 3,755,272 | A | * | 8/1973 | Blank | ........................ 260/80.78 |
| 4,190,562 | A | * | 2/1980 | Westerman | ............... 526/318.5 |
| 4,338,239 | A | * | 7/1982 | Dammann | ................... 524/549 |
| 4,384,096 | A | * | 5/1983 | Sonnabend | .................. 526/313 |
| 4,892,916 | A | * | 1/1990 | Hawe et al. | .................. 526/304 |
| 5,504,162 | A | * | 4/1996 | Friedrich et al. | ......... 525/328.2 |
| 5,506,325 | A | * | 4/1996 | Swarup et al. | .......... 526/318.41 |

FOREIGN PATENT DOCUMENTS

| DE | 3925220 | * | 1/1991 |
| EP | 047 009 | | 3/1982 |
| EP | 0047009 | * | 3/1982 |
| EP | 328 725 | | 8/1989 |
| EP | 335 624 | | 10/1989 |
| EP | 435 066 | | 7/1991 |
| SU | 428347 | * | 4/1975 |

OTHER PUBLICATIONS

*Enc. of Polymer Science and Engineering*, vol. 17, pp. 462-468, 1989.

* cited by examiner

*Primary Examiner*—Bernard Lipman
(74) *Attorney, Agent, or Firm*—Novak Druce + Quigg LLP

(57) ABSTRACT

The use of copolymers obtainable by the radically initiated polymerization of A) 50 to 99.9 wt % of an olefinically unsaturated C3 to C5 monocarboxylic acid, an olefinically unsaturated C4 to C8 dicarboxylic acid or its anhydride, or a mixture of such carboxylic acids or carboxylic acid anhydrides with B) 0.1 to 50 wt % of one or more long-chained compounds with isolated multiple C—C bonds from the group (1) mono or polyunsaturated C8 to C30 monocarboxylic acids which may have additional hydroxyl groups and their alkaline metal and earth alkaline metal salts, alkyl esters, amides, sorbitane esters, glycerin esters and polyglycerin esters, (2) mono or polyunsaturated aliphatic Ca to C30 amines, (3) mono or polyunsaturated C8 to C30 alcohols and esters thereof with saturated Cl to C4 monocarboxylic acids, (4) to (C8 to C30 alkyl) vinyl ether which may incorporate up to 25 alkylene oxide units, and (5) final and medium-position Ci3 to C30 alkenes; C) 0 to 49.9 wt % of other copolymerizable monomers, and D) 0 to 10 wt % of one or more compounds with at least two olefinically unsaturated groups in the molecule as cross-linking agents, as thickening or dispersing agents, especially in cosmetic and pharmaceutical preparations.

8 Claims, No Drawings

USE OF COPOLYMERS OF CARBOXYLIC ACIDS AND LONG-CHAIN COMPOUNDS WITH ISOLATED C-C MULTIPLE BONDS AS THICKENERS OR DISPERSANTS

The present invention relates to the use of copolymers of carboxylic acids and long-chain compounds with isolated C—C multiple bonds, with or without other copolymerizable monomers and crosslinkers, as thickeners or dispersants, eg. in cosmetic or pharmaceutical preparations, and to cosmetic or pharmaceutical preparations containing these copolymers. Since some of the copolymers are novel substances, the invention also relates to these novel copolymers.

Conventional thickeners or viscosity regulators are copolymers of olefinically unsaturated carboxylic acids such as (meth)acrylic acid, maleic acid or maleic anhydride and hydrophobic comonomers such as (meth)acrylic esters, α-olefins with 2-12 carbon atoms or vinyl ethers such as vinyl methyl ether, with or without small amounts of a crosslinker. Copolymers of these types are described, for example, in EP-A 328 725 (1) and EP-A 435 066 (2).

U.S. Pat. No. 3,755,272 (3) discloses copolymers of unbranched α-olefins with 8-30 carbon atoms and (meth)acrylic acid. These copolymers are suitable for producing electrodeposition paints, water-soluble surface coatings, floor coverings and textile-treating compositions.

EP-A 0 47 009 (4) relates to copolymers of 70-93% by weight of partly or completely neutralized acrylic acid and 7-30% by weight of an α-olefin with 6-18 carbon atoms, with or without small amounts of a crosslinker. These copolymers are used as water-absorbing material in the form of, for example, films, fibers or fabrics in the medical and body care sectors. The copolymer is also recommended as flocculant in water treatment.

EP-A 0 335 624 discloses surface-active polymers suitable as thickeners which are composed of from 0.5 to 50% by weight of ionic, non-ionic or ampholytic α,β-unsaturated monomers having at least one aliphatic or araliphatic lipophilic group of 8 to 30 carbon atoms, and of from 40 to 99% by weight of further non-lipophilic α,β-unsaturated monomers. The lipophilic monomers are predominantly ionic monomers, but also non-ionic (meth)acrylates or allyl ether compounds.

The thickeners or viscosity regulators disclosed in the prior art have a number of disadvantages. Thus, these compositions are often insufficiently stable to hydrolysis and tend to decompose under the conditions of use. Some of these compositions have a not inconsiderable potential toxicity, which is particularly important for cosmetic use. Moreover the stability of the cosmetic preparations produced with these compositions, in particular of emulsions, is still not optimal, the stability to electrolytes in particular requiring improvement.

It is an object of the present invention to provide novel thickeners and dispersants for cosmetic preparations which no longer have the prior art disadvantages described.

We have found that this object is achieved by using copolymers which are obtainable by free-radical polymerization of
A) 50-99.9% by weight of an olefinically unsaturated $C_3$-$C_5$-monocarboxylic acid, of an olefinically unsaturated $C_4$-$C_8$-dicarboxylic acid or of its anhydride or a mixture of such carboxylic acids or anhydrides with
B) 0.1-50% by weight of one or more long-chain compounds with isolated C—C multiple bonds from the group comprising
   (1) mono- or polyunsaturated $C_8$-$C_{30}$-monocarboxylic acids which may have additional hydroxyl groups, as well as their alkali metal and alkaline earth metal salts, alkyl esters, amides, sorbitan esters, glycerol esters or polyglycerol esters,
   (2) mono- or polyunsaturated aliphatic $C_8$-$C_{30}$-amines,
   (3) mono- or polyunsaturated $C_8$-$C_{30}$-alcohols as well as their esters with saturated $C_1$-$C_4$-monocarboxylic acids,
   (4) $C_8$-$C_{30}$-alkyl vinyl ethers which may contain up to alkylene oxide units incorporated, and
   (5) terminal and internal $C_{16}$-$C_{30}$-alkenes,
C) 0-49.9% by weight of other copolymerizable monomers and
D) 0-10% by weight of one or more compounds with at least two olefinically unsaturated groups in the molecule as crosslinkers, as thickeners or dispersants.

In a preferred embodiment, the copolymer used according to the invention is composed of
A) 75-99.45% by weight, in particular 94-98.9% by weight, of the carboxylic acid component A,
B) 0.5-24.95% by weight, in particular 1-5.9% by weight, of the long-chain compounds with isolated C—C multiple bonds B,
C) 0-24.45% by weight, in particular 0-4.9% by weight, of other copolymerizable monomers and
D) 0.05-5% by weight, in particular 0.1-2.5% by weight, of the crosslinker component D.

Particularly suitable as component A are acrylic acid, methacrylic acid or maleic anhydride, but also crotonic acid, 2-pentenoic acid, maleic acid, fumaric acid or itaconic acid.

Long-chain compounds with isolated C—C multiple bonds B mean those with isolated acetylenic triple bonds and, in particular, those with isolated olefinic double bonds. "Isolated" means that when a plurality of such C—C multiple bonds are present they are not conjugated and do not interact with functional groups with π electron systems, eg. carboxyl or carbonyl groups, either.

Particularly suitable long-chain carboxylic acids (1) for component B are naturally occurring unsaturated fatty acids, for example oleic acid, nervonic acid, α-hydroxynervonic acid, elaidic acid, erucic acid, stearolic acid, palmitoleic acid, vaccenic acid, linoleic acid, linolenic acid, petroselinic acid, arachidonic acid or ricinoleic acid. Of these, $C_{14}$-$C_{24}$-monocarboxylic acids with 1-4 C—C multiple bonds, in particular olefinic double bonds, are preferred. The carboxylic acids (1) can be used in the form of the acid or as alkali metal salts, especially sodium or potassium salts, or as alkaline earth metal salts, in particular as calcium salts.

Esters of long-chain carboxylic acids (1) which are used are the $C_1$-$C_4$-alkyl esters such as the methyl, ethyl, n-propyl, n-butyl or tert-butyl esters, eg. methyl oleate, the esters of long-chain $C_{14}$-$C_{24}$-alcohols with 1-4 C—C multiple bonds, in particular olefinic double bonds, such as oleyl oleate, sorbitan esters such as sorbitan monooleate or sesquioleate and the glycerol and polyglycerol esters, eg. mono-, di- and triglycerides such as glycerol trioleate, that is to say including naturally occurring fats (lipids).

Also suitable are amides of the carboxylic acids described and numerous amines, for example oleic acid diethanolamide, isopropanolamide or dibutylamide.

Particularly suitable long-chain amines (2) for component B are aliphatic primary $C_{14}$-$C_{24}$-amines with 1-4 C—C multiple bonds, in particular olefinic double bonds, eg. oleylamine.

Long-chain alcohols (3) particularly used for component B are primary $C_{14}$-$C_{24}$-alcohols with 1-4 C—C multiple bonds, in particular olefinic double bonds, as well as esters thereof with saturated $C_1$-$C_4$-monocarboxylic acids such as formic acid, acetic acid, propionic acid or butyric acid. Examples of (3) are oleyl alcohol and oleyl acetate.

Likewise very suitable as component B are oils of natural origin, in particular oils of vegetable origin, as well as natural waxes and animal tallows, fats and greases which contain the said compounds (1) to (3). Suitable examples thereof are coconut, palm kernel, palm, peanut, soybean, rape, sunflower, igoba, olive, sesame, cottonseed, linseed, safflower, corn, castor or fish oil.

Examples of long-chain alkyl vinyl ethers (4) which may contain up to 25, preferably up to 10, in particular up to 7, alkylene oxide units, eg. ethylene oxide, propylene oxide or butylene oxide units or mixtures thereof, incorporated are n-octyl vinyl ether, 2-ethylhexyl vinyl ether, n-nonyl vinyl ether, isononyl vinyl ether, n-decyl vinyl ether, n-dodecyl vinyl ether, n-tridecyl vinyl ether, isotridecyl vinyl ether, n-tetradecyl vinyl ether, n-hexadecyl vinyl ether, n-octadecyl vinyl ether, n-eicosyl vinyl ether or octadecyl heptaethyleneoxy-vinyl ether. $C_{10}$-$C_{25}$-alkyl vinyl ethers are particularly preferred.

Particularly suitable long-chain terminal and internal alkenes (5) are terminal $C_{16}$-$C_{24}$-alkenes (α-olefins). Examples of (5) are 1-hexadecene, 1-octadecene, 1-eicosene, 1-tetracosene as well as $C_{20}/C_{24}$ and $C_{20}/C_{30}$ mixtures or cuts of the corresponding olefin fractions.

Examples of other copolymerizable monomers C suitable for slight modification of the copolymers used according to the invention are n-vinylpyrrolidone, n-vinylcaprolactam, $C_1$-$C_{18}$-alkyl (meth)acrylates, eg. methyl (meth)acrylate, ethyl (meth)acrylate or stearyl (meth)acrylate, (meth)acrylamide or N—($C_1$-$C_{18}$ alkyl)(meth)acrylamides, eg. N,N-dimethyl(meth)acrylamide, N-tertbutyl(meth)acrylamide or N-tert-octyl(meth)acrylamide, vinyl esters of $C_1$-$C_{18}$-carboxylic acids, eg. vinyl acetate, vinyl propionate, vinyl versatate, hydroxyalkylene mono(meth)acrylates with two to six carbon atoms in the alkylene chain or (meth)acrylates of polyethylene glycol monomethyl and monoethyl ethers with 1-25 ethylene oxide units in the molecule, eg. ethyl diglycol acrylate.

Used as crosslinker component D are olefinically polyunsaturated compounds such as, in particular, divinylbenzene, divinylethyleneurea, diallyltartaramide, methylenebisacrylamide, (meth)acrylates of polyfunctional alcohols such as trimethylolpropane, pentaerythritol, alkylene glycols with 2-6 carbon atoms in the alkylene group, polyethylene glycols or polypropylene glycols, allyl esters of (meth)acrylic acid, oleyl (meth)acrylate, oleyl(meth)acrylamide, trivinylcyclohexane, triallyltriazinetrione and allyl ethers of trimethylolpropane, pentaerythritol and sucrose with at least two allyl ether units per molecule. Pentaerythritol triallyl ether, pentaallylsucrose, allyl methacrylate, trimethylolpropane diallyl ether and methylenebisacrylamide are particularly preferred.

The copolymers used according to the invention can be prepared in principle by polymerizing the monomers A to D by all conventional methods. A particularly suitable method of preparation is precipitation polymerization in which the monomers, but not the polymer, are soluble in the solvent system used. Suitable solvents are aromatic compounds such as toluene or xylene, halogenated compounds such as 1,1,1-trichloroethane or methylene chloride, as well as, in particular, semipolar solvents such as ketones with 3-6 carbon atoms and $C_2$-$C_6$-alkyl esters of formic and acetic acids, furthermore non-polar hydrocarbons, eg. cyclohexane or petroleum ether, as well as mixtures of these solvents. Also particularly suitable are aromatic and aliphatic hydrocarbons with 5-12 carbon atoms in the molecule.

The polymerization is carried out in the presence of a compound which forms free radicals, such as organic azo or peroxo compounds. Examples of suitable initiators are diacyl peroxides such as dilauroyl, didecanoyl and dioctanoyl peroxides or peresters such as tert-butyl peroctanoate, tert-butyl perpivalate, tert-amyl perpivalate or tert-butyl perneodecanoate as well as azo compounds such as dimethyl 2,2'-azobis(isobutyrate), 2,2'-azobis(isobutyronitrile), 2,2'-azobis(2-methylbutyronitrile) or 2,2'-azobis(2,4-dimethylvaleronitrile).

It is possible to add a small amount of water, alcohols, protective colloids, emulsifiers or else relatively large amounts of a base, eg. potassium carbonate, to the polymerization mixture. The molecular weight of the polymers can, if desired, be reduced by adding regulators to the polymerization mixture.

The polymerization process is preferably controlled so that the polymer results in the form of a fine-particle powder which is subjected, if required, to a suitable separation, drying or grinding process.

The aim of the use according to the invention of the copolymers described is in particular to employ these substances as thickeners, gel formers and emulsifiers for industrial, pharmaceutical and, in particular, cosmetic applications, for example in creams, lotions or gels. The described copolymers are very suitable for thickening aqueous systems to form thickened gels once the dispersed polymer has been sufficiently neutralized by adding a base such as triethanolamine, NaOH, KOH, 2-amino-2-methyl-1-propanol, 2-amino-2-methyl-1,3-propanediol, diisopropanolamine or tetrahydroxypropylethylenediamine. The polymers can be used in a similar way to prepare very stable emulsions from a water phase and an oil phase, in particular oil-in-water emulsions. Compared with conventional emulsifiers, in general smaller amounts of the polymer are required in order to obtain permanently stable emulsions.

The present invention furthermore relates to cosmetic preparations which contain the copolymers used according to the invention as thickeners or dispersants in the amounts customary for this purpose, ie. about 0.05-2% by weight.

Some of the copolymers used according to the invention are novel substances, and therefore the invention also relates to copolymers which are obtainable by free-radical polymerization of A) 50-99.9% by weight of an olefinically unsaturated $C_3$-$C_5$-monocarboxylic acid, of an olefinically unsaturated $C_4$-$C_8$-dicarboxylic acid or of its anhydride or a mixture of such carboxylic acids or anhydrides with B) 0.1-50% by weight of one or more long-chain compounds with isolated C—C multiple bonds from the group comprising
   (1) mono- or polyunsaturated $C_8$-$C_{30}$-monocarboxylic acids which may have additional hydroxyl groups, as well as their alkali metal and alkaline earth metal salts, alkyl esters, amides, sorbitan esters, glycerol esters or polyglycerol esters,
   (2) mono- or polyunsaturated aliphatic $C_8$-$C_{30}$-amines,
   (3) mono- or polyunsaturated $C_8$-$C_{30}$-alcohols as well as their esters with saturated $C_1$-$C_4$-monocarboxylic acids, and
   (4) $C_8$-$C_{30}$-alkyl vinyl ethers which may contain up to 25 alkylene oxide units incorporated, C) 0-49.9% by weight of other copolymerizable monomers and D) 0-10% by weight of one or more compounds with at least two olefinically unsaturated groups in the molecule as crosslinkers.

The copolymers used according to the invention have a number of advantages. The chemical nature of the long-chain comonomers B means that the hydrophobic portions of the polymer cannot be removed by hydrolysis; the particular thickening and dispersing action is therefore retained even under strongly hydrolytic conditions. The comonomers B moreover have a distinctly lower potential toxicity than, for example, the acrylate compounds disclosed in the prior art as comonomers.

The synthesis of the copolymers used according to the invention takes place surprisingly well although, on the one hand, alkyl vinyl ethers are known to be prone to cationic autopolymerization or hydrolysis in the presence of acidic compounds and, on the other hand, compounds with isolated olefinic double bonds, especially compounds with internal olefinic double bonds, are regarded as difficult to polymerize under free-radical conditions because under conventional conditions they can often be homopolymerized only inadequately or themselves are known to be regulating components in the polymerization of other monomers.

EXAMPLES

Unless otherwise indicated, percentage data are based on weight.

Example 1

1400 ml of 1,1,1-trichloroethane, 250 g of acrylic acid, 1.5 g of pentaerythritol triallyl ether and 10 g of 1-octadecene were stirred and flushed with nitrogen for 30 min in a 3 l flanged flask. The mixture was heated to 80° C. while stirring under a stream of nitrogen and, after this temperature was reached, 100 ml of 1,1,1-trichloroethane and 0.4 g of dilauroyl peroxide were run in over the course of 3 h. After a further 3 h, the mixture was cooled, and the precipitated product was filtered off, washed with 500 ml of 1,1,1-trichloroethane and dried at 60° C. under reduced pressure.

To determine the gel viscosity, 1.0 g of the polymer was dispersed in 190 ml of water in a beaker. While stirring, 10 ml of a 10% strength triethanolamine solution were added. The viscosity of the resulting gel was determined with a manual viscometer (Haake VT-02) to be 8.0 Pa·s. It was evident when the gel was spread on a glass plate that it was smooth and virtually free of specks.

To check the emulsifiability, 0.4 g of the polymer was weighed into a beaker and dispersed in 30 ml of liquid paraffin. Then 100 ml of water and subsequently 4 ml of a 10% strength triethanolamine solution were added while stirring vigorously. The emulsion was homogenized in a dispersing unit at 8000 rpm for a few s. The viscosity was determined as above to be 17.6 Pa·s. The structure of the emulsion was assessed after 1 h by spreading on a glass plate. The long-term stability was determined by introducing the emulsion into a 100 ml cylinder and evaluating after 14 d. At this time the emulsion showed no tendency to separate.

Examples 2 to 19

Examples 2 to 19 were carried out in a similar way. Table 1 shows the results.

TABLE 1

Composition and viscosities of the copolymers of Examples 2 to 19

| Ex. No. | Comonomer B | Cross-linker D | Solvent [ratio by vol.] | Viscosity [Pa·s] Gel | Emulsion |
|---|---|---|---|---|---|
| 2 | 10 g 1-hexadecene[a] | 1.5 g PETA | cyclohexane | 21.5 | 17.5 |
| 3 | 10 g 1-octadecene | 1.5 g PETA | cyclohexane | 22.0 | 19.5 |
| 4 | 10 g mixture of 60% 1-eicosene and 40% 1-tetracosene | 1.5 g PETA | cyclohexane | 23.0 | 19.0 |
| 5 | 10 g mixture of $C_{24}$-$C_{30}$-1-alkenes of the approximate composition $C_{26}H_{52}$ | 1.5 g PETA | cyclohexane | 24.6 | 19.5 |
| 6 | 10 g 1-octadecene | 1.5 g PETA | isopropyl acetate | 13.5 | 12.0 |
| 7 | 10 g 1-octadecene | 1.5 g PETA | ethyl acetate/cyclohexane (1:1) | 25.0 | 18.5 |
| 8 | 10 g 1-octadecene | 1.5 g PETA | ethyl acetate/cyclohexane (1:3) | 22.5 | 18.0 |
| 9 | 10 g 1-octadecene | 1.5 g PETA | methyl ethyl ketone/cyclohexane (1:1) | 20.5 | 18.0 |
| 10 | 10 g 1-octadecene | 1.5 g pentaallylsucrose | cyclohexane | 21.0 | 19.0 |
| 11 | 10 g 1-octadecene | 1.5 g allyl methacrylate | cyclohexane | 12.0 | 11.5 |
| 12 | 10 g 1-octadecene | 2.0 g PETA | cyclohexane | 19.0 | 17.0 |
| 13 | 10 g 1-octadecene | 1.0 g PETA | cyclohexane | 17.5 | 14.0 |
| 14 | 10 g 1-octadecene | 0.5 g PETA | cyclohexane | 12.3 | 7.8 |
| 15 | 10 g 1-octadecene | 0.2 g PETA | cyclohexane | 5.2 | 3.7 |
| 16 | 40 g 1-octadecene | 1.5 g PETA | cyclohexane | 19.0 | 16.0 |
| 17 | 20 g 1-octadecene | 1.5 g PETA | cyclohexane | 20.0 | 16.0 |
| 18 | 5 g 1-octadecene | 1.5 g PETA | cyclohexane | 19.0 | 16.0 |
| 19 | 1.5 g 1-octadecene | 1.5 g PETA | cyclohexane | 18.5 | 14.1 |

250 g of acrylic acid were employed as component A in all of Examples 2 to 19.
PETA = Pentaerythritol triallyl ether
[a]Half the quantity of acrylic acid was added dropwise over the course of 2 h only after 80° C. had been reached.

Example 20

1400 ml of 1,1,1-trichloroethane, 250 g of acrylic acid, 1.5 g of pentaerythritol triallyl ether and 10 g of oleic acid were stirred and flushed with nitrogen for 30 min in a 3 l flanged flask. The mixture was heated to 80° C. while stirring under a stream of nitrogen and, after this temperature was reached, 100 ml of 1,1,1-trichloroethane and 0.4 g of dilauroyl peroxide were run in over the course of 3 h. After a further 3 h, the mixture was cooled, and the precipitated product was filtered off, washed with 500 ml of 1,1,1-trichloroethane and dried at 60° C. under reduced pressure.

To determine the gel viscosity, 1.0 g of the polymer was dispersed in 190 ml of water in a beaker. While stirring, 10 ml of a 10% strength triethanolamine solution were added. The viscosity of the resulting gel was determined with a manual viscometer (Haake VT-02) to be 8.0 Pa·s. It was evident when the gel was spread on a glass plate that it was smooth and virtually free of specks.

To check the emulsifiability, 0.4 g of the polymer was weighed into a beaker and dispersed in 30 ml of liquid paraffin. Then 100 ml of water and subsequently 4 ml of a 10% strength triethanolamine solution were added while stirring vigorously. The emulsion was homogenized in a dispersing unit at 8000 rpm for a few s. The viscosity was determined as above to be 7.6 Pa·s. The structure of the emulsion was assessed after 1 h by spreading on a glass plate. The long-term stability was determined by introducing the emulsion into a 100 ml cylinder and evaluating after 14 d. At this time the emulsion showed no tendency to separate.

Examples 21 to 61

Examples 21 to 61 were carried out in a similar way. Table 2 shows the results.

TABLE 2

Composition and viscosities of the copolymers of Examples 21 to 61

| Ex. No. | Comonomer B | Crosslinker D | Solvent [ratio by vol.] | Reaction temp. [° C.] | Viscosity [Pa · s] Gel | Emulsion |
|---|---|---|---|---|---|---|
| 21 | 20 g erucic acid | 1.5 g PETA | 1,1,1-trichloroethane | 80 | 10.2 | 5.2 |
| 22 | 20 g oleic acid | 1.5 g PETA | 1,1,1-trichloroethane | 80 | 9.1 | 6.9 |
| 23 | 20 g oleyl alcohol | 1.5 g PETA | 1,1,1-trichloroethane | 80 | 6.5 | 3.8 |
| 24 | 20 g oleylamine | 1.5 g PETA | 1,1,1-trichloroethane | 80 | 8.5 | 11.3 |
| 25 | 20 g methyl oleate | 1.5 g PETA | 1,1,1-trichloroethane | 80 | 9.1 | 7.9 |
| 26 | 20 g oleyl acetate | 1.5 g PETA | 1,1,1-trichloroethane | 80 | 8.6 | 8.7 |
| 27 | 20 g linoleic acid | 1.5 g PETA | 1,1,1-trichloroethane | 80 | 4.3 | 2.5 |
| 28 | 14 g oleic acid | 1.5 g PETA | cyclohexane | 80 | 15.1 | 9.0 |
| 29 | 14 g olive oil | 1.5 g PETA | cyclohexane | 80 | 19.0 | 13.4 |
| 30 | 14 g rape oil | 1.5 g PETA | cyclohexane | 80 | 12.6 | 7.4 |
| 31 | 14 g linseed oil | 1.5 g PETA | cyclohexane | 80 | 2.8 | 2.9 |
| 32 | 14 g sunflower oil | 1.5 g PETA | cyclohexane | 80 | 15.3 | 9.2 |
| 33 | 14 g soybean oil | 1.5 g PETA | cyclohexane | 80 | 12.7 | 6.7 |
| 34 | 14 g oleic acid | 1.5 g PETA | ethyl acetate/cyclohexane (1:3) | 80 | 14.3 | 8.6 |
| 35 | 14 g oleic acid | 1.5 g PETA | ethyl acetate/cyclohexane (1:1) | 80 | 12.9 | 8.4 |
| 36 | 14 g oleic acid | 1.5 g PETA | ethyl acetate | 80 | 11.8 | 7.9 |
| 37 | 14 g oleic acid | 1.5 g PETA | isopropyl acetate | 80 | 13.1 | 9.1 |
| 38 | 14 g oleic acid | 1.5 g PETA | methyl ethyl ketone/cyclohexane (1:2) | 80 | 11.2 | 6.2 |
| 39 | 14 g oleic acid | 1.5 g PETA | n-hexane | 80 (under 1.5 bar) | 13.3 | 7.0 |
| 40 | 14 g oleic acid | 1.5 g pentaallyl-sucrose | cyclohexane | 80 | 13.2 | 8.1 |
| 41 | 14 g oleic acid | 1.5 g allyl methacrylate | cyclohexane | 80 | 9.0 | 6.7 |
| 42 | 14 g oleic acid | 1.5 g trimethylol propane diallyl ether | cyclohexane | 80 | 10.1 | 4.9 |
| 43 | 14 g oleic acid | 0.3 g methylene-bisacrylamide | cyclohexane | 80 | 4.9 | 3.2 |
| 44 | 14 g oleic acid | 1.8 g PETA | cyclohexane | 80 | 10.8 | 6.7 |
| 45 | 14 g oleic acid | 1.2 g PETA | cyclohexane | 80 | 14.7 | 9.1 |
| 46 | 14 g oleic acid | 0.9 g PETA | cyclohexane | 80 | 11.1 | 7.2 |
| 47 | 14 g oleic acid | 0.6 g PETA | cyclohexane | 80 | 7.4 | 4.3 |
| 48 | 14 g oleic acid | 0.3 g PETA | cyclohexane | 80 | 5.2 | 3.6 |
| 49 | 14 g oleic acid | — | cyclohexane | 80 | 2.2 | 2.9 |
| 50 | 40 g oleic acid | 1.5 g PETA | cyclohexane | 80 | 12.5 | 8.3 |
| 51 | 10 g oleic acid | 1.5 g PETA | cyclohexane | 80 | 12.9 | 14.3 |
| 52 | 6 g oleic acid | 1.5 g PETA | cyclohexane | 80 | 11.7 | 9.2 |
| 53 | 14 g oleic acid | 1.5 g PETA | cyclohexane | 80 | 11.3 | 5.1 |
| 54 | 14 g oleic acid | 1.5 g PETA | cyclohexane | 80[a] | 14.1 | 7.7 |
| 55 | 14 g oleic acid | 1.5 g PETA | cyclohexane | 80[b] | 12.5 | 8.6 |
| 56 | 14 g oleic acid | 1.5 g PETA | cyclohexane | 80[c] | 9.2 | 10.1 |
| 57 | 14 g oleic acid | 1.5 g PETA | cyclohexane | 60[d] | 10.0 | 7.2 |
| 58 | 20 g oleyl alcohol | 1.5 g PETA[e] | 1,1,1-trichloroethane | 80 | 16.2 | 11.4 |
| 59 | 20 g oleyl alcohol | 1.5 g PETA 2 g TGO | 1,1,1-trichloroethane | 80 | 19.1 | 10.5 |
| 60 | 20 g oleyl alcohol | 1.5 g PETA[f] | 1,1,1-trichloroethane | 80 | 11.9 | 4.9 |
| 61 | 20 g oleyl alcohol | 1.5 g PETA[g] | 1,1,1-trichloroethane | 80 | 11.7 | 6.3 |

250 g of acrylic acid were employed as component A in all of Examples 21 to 61.
PETA = Pentaerythritol triallyl ether,
TGO = Dioleyl ester of a polyglycerol ether with a degree of polymerization of 3
[a] 0.2 g dilauroyl peroxide as initiator
[b] 1.2 g dilauroyl peroxide as initiator
[c] 0.6 g dimethyl 2,2'-azobis(isobutyrate) as initiator
[d] 0.4 g tert-butyl perneodecanoate as initiator
[e] 2 g styrene/maleic anhydride copolymer (90:10/$M_w$ = 2000) added
[f] 10 g potassium carbonate added
[g] 2 g water added

Example 62

1400 ml of 1,1,1-trichloroethane, 250 g of acrylic acid, 1.5 g of pentaerythritol triallyl ether and 10 g of octadecyl vinyl ether were stirred and flushed with nitrogen for 30 min in a 3 l flanged flask. The mixture was heated to 80° C. while stirring under a stream of nitrogen and, after this temperature was reached, 100 ml of 1,1,1-trichloroethane and 0.4 g of dilauroyl peroxide were run in over the course of 3 h. After a further 3 h, the mixture was cooled, and the precipitated product was filtered off, washed with 500 ml of 1,1,1-trichloroethane and dried at 60° C. under reduced pressure.

To determine the gel viscosity, 1.0 g of the polymer was dispersed in 190 ml of water in a beaker. While stirring, 10 ml of a 10% strength triethanolamine solution were added. The viscosity of the resulting gel was determined with a manual viscometer (Haake VT-02) to be 10.0 Pa·s. It was evident when the gel was spread on a glass plate that it was smooth and virtually free of specks.

To check the emulsifiability, 0.4 g of the polymer was weighed into a beaker and dispersed in 30 ml of liquid paraffin. Then 100 ml of water and subsequently 4 ml of a 10% strength triethanolamine solution were added while stirring vigorously. The emulsion was homogenized in a dispersing unit at 8000 rpm for a few s. The viscosity was determined as above to be 8.0 Pa·s. The structure of the emulsion was assessed after 1 h by spreading on a glass plate. The long-term stability was determined by introducing the emulsion into a 100 ml cylinder and evaluating after 14 d. At this time the emulsion showed no tendency to separate.

Examples 63 to 75

Examples 63 to 75 were carried out in a similar way. Table 3 shows the results.

We claim:
1. A cosmetic or pharmaceutical composition, containing as a thickener or dispersant an effective amount of a copolymer obtained by free radical polymerization of
   A) 75-99.45% by weight of an olefinically unsaturated $C_3$-$C_5$-monocarboxylic acid, of an olefinically unsaturated $C_4$-$C_8$-dicarboxylic acid or of its anhydride or a mixture of such carboxylic acids or anhydrides with
   B) 0.5-24.95% by weight of one or more long-chain compounds with isolated C—C multiple bonds selected from the group consisting of
      (1) mono- or polyunsaturated $C_8$-$C_{30}$-monocarboxylic acids which may have additional hydroxyl groups, as well as their alkali metal and alkaline earth metal salts, alkyl esters, amides, sorbitan esters, glycerol esters or polyglycerol esters,
      (2) mono- or polyunsaturated aliphatic $C_8$-$C_{30}$-amines, and
      (3) mono- or polyunsaturated $C_8$-$C_{30}$-alcohols as well as their esters with saturated $C_1$-$C_4$-monocarboxylic acids,
   C) 0-24.45% by weight of other copolymerizable monomers and
   D) 0.05-5% by weight of one or more compounds with at least two olefinically unsaturated groups in the molecule as crosslinkers.
2. A composition as defined in claim 1, wherein the copolymers have been prepared using acrylic acid, methacrylic acid or maleic anhydride as component A.
3. A composition as defined in claim 1, wherein the copolymers have been prepared using as component B one or more long-chain compounds with isolated double bonds selected from the group consisting of

TABLE 3

Composition and viscosities of the copolymers of Examples 63 to 75

| Ex. No. | Comonomer B | Crosslinker D | Solvent [ratio by vol.] | Viscosity [Pa·s] Gel | Viscosity [Pa·s] Emulsion |
|---|---|---|---|---|---|
| 63 | 10 g octadecyl vinyl ether | 1.5 g PETA | cyclohexane | 19.0 | 10.0 |
| 64 | 10 g dodecyl vinyl ether | 1.5 g PETA | cyclohexane | 15.0 | 10.0 |
| 65 | 10 g octadecyl heptaethylenoxy-vinyl ether | 1.5 g PETA | cyclohexane | 15.0 | 8.5 |
| 66 | 10 g octadecyl vinyl ether | 1.5 g PETA | isopropyl acetate | 13.0 | 11.0 |
| 67 | 10 g octadecyl vinyl ether | 1.5 g PETA | ethyl acetate/ cyclohexane (1:1) | 16.0 | 8.0 |
| 68 | 10 g octadecyl vinyl ether | 1.5 g pentaallylsucrose | cyclohexane | 21.0 | 13.0 |
| 69 | 10 g octadecyl vinyl ether | 1.5 g allyl methacrylate | cyclohexane | 12.0 | 9.5 |
| 70 | 10 g octadecyl vinyl ether | 2.0 g PETA | cyclohexane | 17.0 | 12.0 |
| 71 | 10 g octadecyl vinyl ether | 1.0 g PETA | cyclohexane | 16.5 | 14.0 |
| 72 | 10 g octadecyl vinyl ether | 0.5 g PETA | cyclohexane | 12.5 | 7.0 |
| 73 | 20 g octadecyl vinyl ether | 1.5 g PETA | cyclohexane | 14.0 | 9.0 |
| 74 | 5 g octadecyl vinyl ether | 1.5 g PETA | cyclohexane | 28.0 | 16.0 |
| 75 | 1.5 g octadecyl vinyl ether | 1.5 g PETA | cyclohexane | 21.0 | 15.0 |

250 g of acrylic acid were employed as component A in all of Examples 63 to 75.
PETA = Pentaerythritol triallyl ether (1) mono- to tetraunsaturated $C_{14}$-$C_{24}$-monocarboxylic acids, as well as their alkali metal and alkaline earth metal salts, $C_1$-$C_4$-alkyl esters, glycerol esters or polyglycerol esters, (2) mono- to tetraunsaturated aliphatic primary $C_{14}$-$C_{24}$-amines, and (3) mono- to tetraunsaturated primary $C_{14}$-$C_{24}$-alcohols as well as their esters with saturated $C_1$-$C_4$-monocarboxylic acids.

4. A composition as defined in claim 1, wherein the copolymers are used which have been prepared using as component D allyl ethers of pentaerythriol, trimethylolpropane or sucrose with at least two allyl ether unita in the molecule as well as alkylether methacrylate, oleyl (meth)acrylate or methylenebisacrylamide.

5. A copolymer obtained by free-radical polymerization of
A) 75-99.45% by weight of an olefinically unsaturated $C_3$-$C_5$-monocarboxylic acid, of an olefinically unsaturated $C_4$-$C_8$-dicarboxylic acid or of its anhydride or a mixture of such carboxylic acids or anhydrides with
B) 0.5-24.95% by weight of one or more long-chain compounds with isolated C—C multiple bonds selected from the group consisting of (1) mono- to tetraunsaturated $C_{14}$-$C_{30}$-monocarboxylic acids as well as their alkali metal and alkaline earth metal salts, $C_1$-$C_4$-alkyl esters, glycerol esters or polyglycerol esters, (2) mono- or polyunsaturated aliphatic CB-$C_{30}$-amines, and (3) mono- or polyunsaturated $C_8$-$C_{30}$-alcohols as well as their esters with saturated $C_1$-$C_4$-monocarboxylic acids, C) 0-24.95% by weight of other copolymerizable monomers and D) 0.05-5% by weight of one or more compounds with at least two olefinically unsaturated groups in the molecule as crosslinkers.

6. A composition as defined in claim 1, wherein component D) is different than component B).

7. A composition as defined in claim 1, wherein component D) is different than component C).

8. A composition as defined in claim 6, wherein component D) is different than component C).

* * * * *